United States Patent [19]
Lee et al.

[11] Patent Number: 6,093,744
[45] Date of Patent: Jul. 25, 2000

[54] N-ACYL SULFAMIC ACID ESTERS USEFUL AS HYPOCHOLESTEROLEMIC AGENTS

[75] Inventors: Helen Tsenwhei Lee, Ann Arbor; Joseph Armand Picard, Canton; William Howard Roark; Bruce David Roth, both of Ann Arbor; Drago Robert Sliskovic, Saline, all of Mich.

[73] Assignee: Warner-Lambert Company, Morris Plains, N.J.

[21] Appl. No.: 09/117,748

[22] PCT Filed: Apr. 21, 1997

[86] PCT No.: PCT/US97/06725

§ 371 Date: Aug. 10, 1998

§ 102(e) Date: Aug. 10, 1998

[87] PCT Pub. No.: WO97/44314

PCT Pub. Date: Nov. 27, 1997

Related U.S. Application Data

[60] Provisional application No. 60/017,882, May 17, 1996.
[51] Int. Cl.$^7$ .......................... A01N 41/06; A01K 31/18; C07C 303/00; C07C 307/00
[52] U.S. Cl. .............................. 514/602; 514/605; 560/12
[58] Field of Search .................................... 514/602, 605; 560/12

[56] References Cited

U.S. PATENT DOCUMENTS

| | | | |
|---|---|---|---|
| 4,657,929 | 4/1987 | Ince et al. | 514/524 |
| 5,053,072 | 10/1991 | Ort et al. | 71/92 |
| 5,245,068 | 9/1993 | Picard et al. | 558/49 |
| 5,254,589 | 10/1993 | Picard et al. | 514/592 |
| 5,324,710 | 6/1994 | Ort et al. | 504/239 |
| 5,491,172 | 2/1996 | Lee et al. | 514/602 |
| 5,633,287 | 5/1997 | Lee et al. | 514/602 |

FOREIGN PATENT DOCUMENTS

| | | |
|---|---|---|
| 0467183 | 1/1992 | European Pat. Off. . |
| 9207826 | 5/1992 | WIPO . |
| 9426702 | 11/1994 | WIPO . |

OTHER PUBLICATIONS

Sliskovic et al., "Inhibitors of Acyl–Co–A:cholesterol O–Acyl Transferase (ACAT) as Hypocholesterolemic Agents. 6. The First Water–Soluble ACAT Inhibitor with Lipid–Regulating Activity", *J. Med. Chem.*, vol. 37, 1994, pp. 560–562.

*Primary Examiner*—Mukund J. Shah
*Assistant Examiner*—Tamthom N. Truong
*Attorney, Agent, or Firm*—Elizabeth M. Anderson

[57] ABSTRACT

The instant invention is new compounds of Formula I

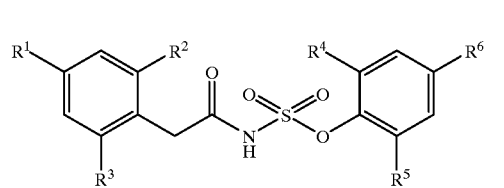

their use as cerebrovascular agents in diseases such as stroke, peripheral vascular disease, restenosis, and as agents for regulating plasma cholesterol concentrations, for treating hypercholesterolemia and atherosclerosis, and for lowering the serum or plasma level of Lp(a). A pharmaceutical composition is also claimed.

16 Claims, No Drawings

N-ACYL SULFAMIC ACID ESTERS USEFUL AS HYPOCHOLESTEROLEMIC AGENTS

This is a national filing of PCT/US97/06725 filed Apr. 21, 1997, claiming priority from U.S. Provisional Application No. 60/017,882 filed May 17, 1996.

BACKGROUND OF INVENTION

This invention relates to chemical compounds having pharmacological activity, to pharmaceutical compositions which include these compounds, and to pharmaceutical methods of treatment using the compounds. More particularly, this invention concerns certain N-acyl sulfamic acid esters with improved physical properties which inhibit the enzyme and acyl-coenzyme A:cholesterol acyltransferase (ACAT).

The compounds of the instant invention show increased chemical stability over those of U.S. Pat. No. 5,245,068.

The compounds of the instant invention show improved physical properties (such as aqueous solubility, decreased lipophilicity, and improved dissolution rates) over those disclosed in U.S. Pat. No. 5,491,172.

U.S. patent application Ser. No. 60/003,03 filed Aug. 3, 1995, teaches other methods of using the compounds taught in U.S. Pat. No. 5,491,172. Both of these are incorporated herein by reference.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme, acyl-CoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

The present invention relates to methods of using the novel compounds to lower plasma cholesterol and/or lipoprotein(a), Lp(a), and more particularly to methods and agents to lower their plasma concentrations to achieve therapeutic benefit.

SUMMARY OF THE INVENTION

The present invention is compounds of the formula

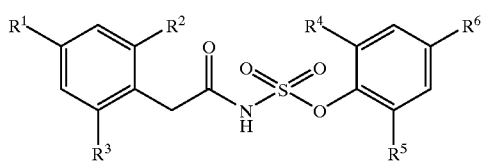

or a pharmaceutically acceptable salt thereof wherein:

$R^1$ is hydrogen, alkyl, or alkoxy;

$R^2$ to $R^5$ are alkyl, alkoxy, or unsubstituted or substituted phenyl;

$R^6$ is —CN—,
—$(CH_2)_{0-1}$—$NR^7R^8$,
—O—$(CH_2)_{1-10}$—Z wherein Z is —$NR^9R^{10}$, $OR^1$, or $CO_2R^1$,
—OC(=O)$R^{11}$,
—$SR^{11}$,
—SCN,
—$S(CH_2)_{1-10}Z$,
—$S(O)_{1-2}R^{12}$ wherein $R^{12}$ is hydroxy, alkoxy, alkyl, $(CH_2)_{1-10}Z$ or $NR^7R^8$;
—C(=O)$XR^{11}$,
—$CH_2$—$R^{13}$ wherein $R^{13}$ is $(CH_2)_{0-5}$—Y—$(CH_2)_{0-5}Z$, or
alkyl of from 1 to 20 carbons with from 1–3 double bonds, which alkyl is optionally substituted by one or more moieties selected from —CN, $NO_2$, halogen, $OR^1$, $NR^9R^{10}$, and $CO_2R^1$;

wherein $R^7$ and $R^8$ are each independently selected from:
-hydrogen, at least one of $R^7$ and $R^8$ is other than hydrogen,
—$(CH_2)_{1-10}Z$ wherein Z is as defined above and $R^9$ and $R^{10}$ are each independently selected from hydrogen, alkyl, and unsubstituted or substituted phenyl, or
$R^9$ and $R^{10}$ are taken together with the nitrogen to which they are attached to form a ring selected from:
—$(CH_2)_2$—O—$(CH_2)_2$,
—$(CH_2)_2$—S—$(CH_2)_2$,
—$(CH_2)_2$—$CR^{14}R^{15}$—$(CH_2)_{1-2}$, and
—$(CH_2)_2$—$NR^{16}$—$(CH_2)_2$, wherein $R^{14}$, $R^{15}$, and $R^{16}$ are each independently selected from hydrogen, alkyl, and unsubstituted or substituted phenyl;
—C(=Q)$XR^{11}$ wherein X is a bond or NH wherein Q is O or S, $R^{11}$ is hydrogen, alkyl, unsubstituted or substituted phenyl,
—$(CH_2)_{0-5}$—Y—$(CH_2)_{0-5}Z$ wherein Z is as defined above and Y is phenyl or a bond;
—C(=O)—$CR^{17}R^{18}Z$;
—C(=O)NHC$R^{17}R^{18}Z$ wherein $R^{17}$ and $R^{18}$ are each independently hydrogen, alkyl, phenyl, substituted phenyl, or the side chain of a naturally occurring amino acid;
—$S(O)_{1-2}R^{19}$ wherein $R^{19}$ is alkyl, unsubstituted or substituted phenyl, naphthyl, or a heteroaromatic ring, or $NR^9R^{10}$ or
$R^7$ and $R^8$ are taken together with the nitrogen to which they are attached to form a ring:
—$(CH_2)_2$—O—$(CH_2)_2$—,
—$(CH_2)_2$—S—$(CH_2)_2$—,
—$(CH_2)_2$—$CR^{14}R^{15}$—$(CH_2)_{1-2}$—, —(CH$_2$)$_2$—NR$^{16}$—(CH$_2$)$_2$— wherein R$^{14}$, R$^{15}$, and R$^{16}$ are as above.

Preferred compounds of the invention are those of Formula I wherein:

R$^1$ is hydrogen or alkyl of from 1 to 4 carbon atoms;
R$^2$ to R$^5$ are each alkyl of from 1 to 4 carbon atoms;
R$^6$ is —NR$^7$R$^8$ wherein R$^7$ and R$^8$ are each independently selected from:
hydrogen, at least one of R$^7$ and R$^8$ is not hydrogen,
—(CH$_2$)$_{1-10}$Z,
—C(=Q)XR$^{11}$, or
—S(O)$_{1-2}$R$^{19}$.

More preferred compounds are those of Formula I wherein

R$^7$ is hydrogen and
R$^8$ is —C(=O)CR$^{17}$R$^{18}$Z wherein Z is NH$_2$ where one of R$^{17}$ and R$^{18}$ is the side chain of a naturally occurring amino acid and the other is hydrogen.

Other preferred compounds are those of Formula I wherein:

R$^1$ is hydrogen or alkyl of from 1 to 4 carbon atoms;
R$^2$ to R$^5$ are each alkyl of from 1 to 4 carbon atoms;
R$^6$ is NR$^7$R$^8$ wherein R$^7$ and R$^8$ taken together with the nitrogen to which they are attached to form a ring:
—(CH$_2$)$_2$—O—(CH$_2$)$_2$—,
—(CH$_2$)$_2$—S—(CH$_2$)$_2$—,
—(CH$_2$)$_2$—CR$^{14}$R$^{15}$—(CH$_2$)$_2$— wherein R$^{14}$ and R$^{15}$ are each independently selected from hydrogen, alkyl, or phenyl, or
—(CH$_2$)$_2$—NR$^{16}$—(CH$_2$)$_2$— wherein R$^{16}$ is hydrogen, alkyl, or phenyl.

Still other preferred compounds are those of Formula I wherein:

R$^1$ is hydrogen or alkyl of from 1 to 4 carbon atoms;
R$^2$ to R$^5$ are each alkyl of from 1 to 4;
R$^6$ is NR$^7$R$^8$ wherein one of R$^7$ and R$^8$ is hydrogen and the other is S(O)$_{1-2}$R$^{19}$.

More preferred compounds are those of Formula I wherein

R$^1$ is hydrogen or alkyl of from 1 to 4 carbons,
R$^2$ to R$^5$ are alkyl of from 1 to 4 carbons, and
R$^6$ is —C(=O)XR$^{11}$ or —CH$_2$R$^{13}$.

Still other preferred compounds are those of Formula I wherein:

R$^1$ is hydrogen or alkyl of from 1 to 4 carbon atoms;
R$^2$ to R$^5$ are alkyl of from 1 to 4 carbon atoms;
R$^6$ is —O—(CH$_2$)$_{1-10}$Z,
—O—C(=O)R$^{11}$,
—SH,
—SCN,
—S(CH$_2$)$_{1-10}$Z, or
—S(O)$_{1-2}$R$^{12}$.

Other preferred compounds are those of Formula I wherein

R$^1$ is hydrogen or alkyl of from 1 to 4 carbon atoms;
R$^2$ to R$^5$ are alkyl of from 1 to 4 carbon atoms;
R$^6$ is O(CH$_2$)$_{1-10}$NR$^9$R$^{10}$.

Especially preferred are:

(S)-[5-tert-Butoxycarbonylamino-5-(3,5-diisopropyl-4-{[(2,4,6-triisopropyl-phenyl)-acetyl]sulfamoyloxy}-phenylcarbamoyl)-pentyl]-carbamic acid tert-butyl ester;

(S)-[(2,4,6-Triisopropyl-phenyl)-acetyl]-sulfamic acid 4-(2,6-diamino-hexanoylamino)-2,6-diisopropyl-phenyl ester dihydrochloride;

[(2,4,6-Triisopropyl-phenyl)-acetyl]-sulfamic acid 4-(2-t-butoxycarbonylamino-acetylamino)-2,6-diisopropyl-phenyl ester;

[(2,4,6-Triisopropyl-phenyl)-acetyl]-sulfamic acid 4-(2-amino-acetylamino)-2,6-diisopropyl-phenyl ester;

[(2,4,6-Triisopropyl-phenyl)-acetyl]-sulfamic acid 4-(2-t-butoxycarbonylamino-4-methylsulfanyl-butyrylamino)-2,6-diisopropyl-phenyl ester;

[(2,4,6-Triisopropyl-phenyl)-acetyl]-sulfamic acid 4-(2-amino-4-methylsulfanyl-butyrylamino)-2,6-diisopropyl-phenyl ester trifluoroacetate;

3-[3-(3,5-Diisopropyl-4-{[(2,4,6-triisopropyl-phenyl)-acetyl]sulfamoyloxy}-phenyl)-ureido]-propionic acid ethyl ester;

3-[3-(3,5-Diisopropyl-4-{[(2,4,6-triisopropyl-phenyl)-acetyl]sulfamoyloxy}-phenyl)-ureido]-propionic acid;

[(2,4,6-Triisopropyl-phenyl)-acetyl]-sulfamic acid 4-[2-amino-3-(1H-indol-3-yl)-propionylamino]-2,6-diisopropyl-phenyl ester;

[(2,4,6-Triisopropyl-phenyl)-acetyl]-sulfamic acid 4-(5-amino-pentanoylamino)-2,6-diisopropyl-phenyl ester trifluoroacetate(1:1)(salt);

(D)-[(2,4,6-Triisopropyl-phenyl)-acetyl]-sulfamic acid 4-(2-amino-propionylamino)-2,6-diisopropyl-phenyl ester trifluoroacetate(1:1)(salt);

(L)-[(2,4,6-Triisopropyl-phenyl)-acetyl]-sulfamic acid 4-(2-amino-propionylamino)-2,6-diisopropyl-phenyl ester;

[(2,4,6-Triisopropyl-phenyl)-acetyl]-sulfamic acid 4-(2-amino-2-methyl-propionylamino)-2,6-diisopropyl-phenyl ester;

[(2,4,6-Triisopropyl-phenyl)-acetyl]-sulfamic acid 4-(3-dimethylamino-propoxy)-2,6-diisopropyl-phenyl ester;

[(2,4,6-Triisopropyl-phenyl)-acetyl]-sulfamic acid 4-(3-dimethylamino-propoxy)-2,6-diisopropyl-phenyl ester hydrochloride salt;

[(2,4,6-Triisopropyl-phenyl)-acetyl]-sulfamic acid 4-(3-amino-propoxy)-2,6-diisopropyl-phenyl ester hydrochloride salt;

[(2,4,6-Triisopropyl-phenyl)-acetyl]-sulfamic acid 2,6-diisopropyl-4-thiocyanato-phenyl ester;

[(2,4,6-Triisopropyl-phenyl)-acetyl]-sulfamic acid 4-cyano-2,6-diisopropyl-phenyl ester;

[(2,4,6-Triisopropyl-phenyl)-acetyl]-sulfamic acid 4-[(2-amino-acetylamino)-methyl]-2,6-diisopropyl-phenyl ester;

[(2,4,6-Triisopropyl-phenyl)-acetyl]-sulfamic acid 4-formyl-2,6-diisopropyl-phenyl ester;

[(2,4,6-Triisopropyl-phenyl)-acetyl]-sulfamic acid 4-(2-cyano-vinyl)-2,6-diisopropyl-phenyl ester;

[(2,4,6-Triisopropyl-phenyl)-acetyl]-sulfamic acid 4-(benzylamino-methyl)-2,6-diisopropyl-phenyl ester mono hydrochloride;

[(2,4,6-Triisopropyl-phenyl)-acetyl]-sulfamic acid 2,6-diisopropyl-4-(4-methyl-piperazin-1-ylmethyl)-phenyl ester, dihydrochloride;

[(2,4,6-Triisopropyl-phenyl)-acetyl]-sulfamic acid 4-carbamoyl-2,6-diisopropyl-phenyl ester;

[(2,4,6-Triisopropyl-phenyl)-acetyl]-sulfamic acid 4-hydroxymethyl-2,6-diisopropyl-phenyl ester;

[(2,4,6-Triisopropyl-phenyl)-acetyl]-sulfamic acid 4-acetylamino-2,6-diisopropyl-phenyl ester;

[(2,4,6-Triisopropyl-phenyl)-acetyl]-sulfamic acid 4-(2-hydroxy-ethylamino)-2,6-diisopropyl-phenyl ester;

[(2,4,6-Triisopropyl-phenyl)-acetyl]-sulfamic acid 4-[bis-(2-hydroxy-ethyl)-amino]-2,6-diisopropyl-phenyl ester;

[(2,4,6-Triisopropyl-phenyl)-acetyl]-sulfamic acid 4-[3-(2,6-diisopropyl-phenyl)-ureido]-2,6-diisopropyl-phenyl ester;

[(2,4,6-Triisopropyl-phenyl)-acetyl]-sulfamic acid 2,6-diisopropyl-4-(3-phenyl-ureido]-phenyl ester;

[(2,4,6-Triisopropyl-phenyl)-acetyl]-sulfamic acid 2,6-diisopropyl-4-(3-phenyl-thioureido]-phenyl ester;

[(2,4,6-Triisopropyl-phenyl)-acetyl]-sulfamic acid 2,6-diisopropyl-4-(thiophene-2-sulfonylamino)-phenyl ester;

[(2,4,6-Triisopropyl-phenyl)-acetyl]-sulfamic acid 4-(5-dimethylamino-naphthalene-1-sulfonylamino)-2,6-diisopropyl-phenyl ester;

[(2,4,6-Triisopropyl-phenyl)-acetyl]-sulfamic acid 2,6-diisopropyl-4-methanesulfonylamino-phenyl ester;

[(2,4,6-Triisopropyl-phenyl)-acetyl]-sulfamic acid 2,6-diisopropyl-4-sulfamoyl-phenyl ester;

6-(3,5-Diisopropyl-4-{[(2,4,6-triisopropyl-phenyl-acetyl]sulfamoyloxy}-phenyl)-hexanoic acid ethyl ester; and 6-(3,5-Diisopropyl-4-{[(2,4,6-triisopropyl-phenyl-acetyl]sulfamoyloxy}-phenyl)-hexanoic acid.

The compounds of the invention are useful in treating cerebrovascular diseases such as stroke, peripheral vascular diseases, and restenosis. They are useful in lowering serum or plasma levels of Lp(a). They are agents for regulating plasma cholesterol concentrations. The compounds are useful in treating hypercholesteremia and atherosclerosis.

Pharmaceutical compositions containing one or more of the compounds are also part of this invention.

Novel intermediates are also part of the invention.

DETAILED DESCRIPTION

The compounds of the present invention provide a novel class of N-acyl sulfamic acid esters (or thioesters), N-acyl sulfonamides, and N-sulfonyl carbamic acid esters (or thioesters) which are ACAT inhibitors, rendering them useful in pharmaceutical treatments. The advantage of the instant invention is the improved physical properties which provide compounds suitable as pharmaceuticals.

In Formula I above, illustrative examples of straight or branched carbon chains having from 1 to 10 carbon atoms include methyl, ethyl, n-propyl, isopropyl, n-butyl, isobutyl, tert-butyl, n-pentyl, isopentyl, n-hexyl, n-heptyl, and n-octyl.

Alkoxy means straight or branched groups having from 1 to 6 carbon atoms include, for example, methoxy, ethoxy, n-propoxy, t-butoxy, and pentyloxy.

The natural (essential) amino acids are: valine, leucine, isoleucine, threonine, methionine, phenylalanine, tryptophan, lysine, alanine, aginine, aspartic acid, cysteine, glutamic acid, glycine, histidine, proline, serine, tyrosine, asparagine, and glutamine.

Preferred natural amino acids are: valine, leucine, isoleucine, threonine, lysine, alanine, glycine, serine, asparagine, and glutamine.

Phenyl, naphthyl, and heteroaromatic rings are unsubstituted or substituted by from 1 to 5 substituents selected from alkyl of from 1 to 6 carbons, alkoxy, halogen, nitro, cyano, carboxylic acids and alkyl esters, amino, and hydroxyl.

Heteroaromatic rings are, for example, 2-, 3-, or 4-pyridinyl; 2-, 4-, or 5-pyrimidinyl; 2- or 3-thienyl; isoquinolines, quinolines, pyrroles, indoles, and thiazoles.

Preferred substituents are halogen, for example, fluoro and chloro, methoxy, and amino.

Pharmaceutically acceptable salts of the compounds of Formula I are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Berge S N, et al, *J. Pharm. Sci.*, 1977;66:1–19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

The ability of the compounds of the present invention to lower Lp(a) is evaluated in the following procedure. Nine male cynomolgus monkeys (*Macaca fascicularis*, 4–5 kg) are maintained on a standard monkey chow diet (containing less than 5 fat and only trace amounts of cholesterol). The diet is available daily from 9 AM until 2 PM. These animals transport approximately equal amounts of cholesterol in HDL (47%) and LDL (51%) and have low triglycerides compared to humans (approximately 50 mg/dL). Five weekly blood samples are taken from anesthetized, restrained animals, and then the animals were dosed with the desired compound daily before meals (for 3 weeks at 30 mg/kg) by incorporating it into oatmeal cream pies (Little Debbie Snack Cakes, McKee Foods, Collegedale, Tenn.). Tang breakfast beverage crystals (Kraft General Foods, Inc., White Plains, N.Y.), and additional cream filling is also added to individual servings. Most animals consume the drug-containing treat immediately since they are without food during the night. They are not given their daily meal until they have consumed the treat. Mean plasma cholesterol (top line) and Lp(a) (bottom line) values are calculated (all values in mg/dL).

The average baseline values for cholesterol and Lp(a) are calculated. Using these values, the percentage decreases for cholesterol and Lp(a) are known. It is important to note that every animal demonstrates a decrease in cholesterol and Lp(a). The decrease in total cholesterol is due primarily to a decrease in LDL-cholesterol.

The compounds of the present invention are thus useful in pharmaceutical formulations for the treatment of stroke, peripheral vascular disease, and restenosis.

In therapeutic use as agents for treating stroke, peripheral vascular disease, and restenosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

As shown by the data presented below in Table 1, the compounds of the present invention are inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field F J, Salone R G, *Biochemica et Biophysica* 1982; 712:557–570. The test assesses the ability of a test compound to inhibit the acylation of cholesterol by oleic acid by measuring the amount of radiolabeled cholesterol oleate formed from radiolabeled oleic acid in a tissue preparation containing rat liver microsomes.

The data appear in Table 1 where they are expressed in $IC_{50}$ values; i.e., the concentration of test compound required to inhibit the activity of the enzyme by 50%.

TABLE 1

| In Vitro Biological Data | |
|---|---|
| Example | LAI ($\mu$M) |
| 1 | 23 |
| 2 | >50 |
| 3 | 18 |
| 4 | 48 |
| 6 | 750 |
| 7 | 49 |
| 8 | >50 |
| 9 | 24 |
| 10 | — |
| 11 | >50 |
| 12 | >50 |
| 13 | >50 |
| 14 | >50 |
| 15 | >50 |
| 16 | >50 |
| 17 | 29 |
| 18 | >50 |
| 19 | >50 |
| 20 | 43.2 |
| 21 | 44.6 |
| 22 | 22.8 |
| 23 | 50 |
| 24 | 43.8 |
| 25 | 38.5 |
| 26 | 30 |
| 27 | 43 |

TABLE 1-continued

| In Vitro Biological Data | |
|---|---|
| Example | LAI ($\mu$M) |
| 28 | 43.8 |
| 29 | 33 |
| 30 | 20.3 |
| 31 | 37.4 |
| 32 | 31.1 |
| 33 | 10.6 |
| 34 | 45 |
| 35 | 50 |
| 36 | 19 |
| 37 | >50 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet (designated PCC) containing 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2.

TABLE 2

| Compound of Example | APCC % Change in Plasma TC (dose in mg/kg) |
|---|---|
| 1 | +7 (1) |
| 2 | −60 (10) |
| 3 | −40 (30) |
| 4 | −65 (10) |
| 6 | −72 (10) |
| 7 | −30 (30) |
| 8 | −15 (10) |
| 9 | −25 (10) |
| 10 | −15 (10) |
| 11 | −19 (10) |
| 12 | −74 (10) |
| 13 | −8 (10) |
| 14 | −11 (10) |
| 15 | −26 (10) |
| 16 | −47 (10) |
| 17 | −46 (10) |
| 18 | −38 (10) |
| 19 | −16 (10) |
| 20 | −44 (10) |
| 21 | −35 (10) |
| 22 | −18 (10) |
| 23 | 5 10) |
| 24 | −5 (10) |
| 25 | −54 (10) |
| 26 | −44 (10) |
| 27 | — |
| 28 | −48 (10) |
| 29 | −3 (10) |
| 30 | −30 (10) |
| 31 | −21 (10) |
| 32 | −60 (10) |
| 33 | −61 (10) |
| 34 | −13 (10) |
| 35 | — |
| 36 | −17 (10) |
| 37 | −47 (10) |

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets or transdermal systems are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

GENERAL SYNTHETIC METHODS

Some intermediates for compounds of the present invention are readily obtainable using the methods set forth in Lee, et al., U.S. Pat. No. 5,491,172. Thus, as shown in Scheme 1, a 4-nitro-phenol (I) is reacted with N-chlorosulfonyl isocyanate at elevated temperatures, and quenched with water to give the 4-nitro sulfamate (II). This is then coupled with the phenyl acetic acid analog (III) using standard coupling techniques (e.g., DCC, CDI, acid chloride, and mixed anhydride) to give the compound (IV). Simple reduction of the nitro group (Raney Nickel/hydrogen) gives the amino compound (V) which can be functionalized to give the compounds of the present invention. For example, alkylating with an activated alkyl group X—(CH$_2$)$_n$NR$^9$R$^{10}$ (where X is halo, triflate, or other similar leaving groups known to those skilled in the art, and n, R$^7$, and R$^8$ have the meanings defined in the scope of Formula I) gives a compound (VI) of the present invention. Similarly, reacting the amino compound (V) with an activated acyl group L—C(O)R$^{11}$ (where L is a group that activates carboxylic acid coupling reactions such as halo, imidazole, mixed anhydride, and R$^{11}$ has the meaning defined in the scope of Formula I) gives an amide compound (VII) of the present invention. The amino compound (V) can also be reacted with activated sulfonyl compounds (LS(O)$_2$R$^{12}$ wherein R$^{12}$ has the meaning defined in the scope of Formula I) to give sulfonamides (VIII) and with di-alkyl compounds (X(CH$_2$)$_2$Z(CH$_2$)$_2$X wherein Z is O, S, NR, or CRR$^1$ and X is halo, triflate, or other similar leaving groups known to those skilled in the art) to give the cyclic compounds (IX).

Synthesis of the corresponding oxygen analogs is shown in Scheme 2. A protected dihydroquinone (X) (where the protecting group can be any of the groups known to those skilled in the art, such as silyl ethers, benzyl ethers, alkyl ethers, and acyl groups) is treated with N-chlorosulfonyl isocyanate at elevated temperatures, and quenched with water to give the sulfamate (XI). This is then coupled with the phenyl acetic acid analog (III) using standard coupling techniques (e.g., DCC, CDI, acid chloride, or mixed anhydride,) to give the compound (XII). Deprotection of the hydroxyl group gives the hydroxy compound (XIII) which can be functionalized to give the compounds of the present invention. For example, alkylating with an activated alkyl group X—(CH$_2$)$_n$NR$^9$R$^{10}$ (where X, n, R$^9$, and R$^{10}$ have the meanings defined in the scope of this patent) gives an ether compound (XIV) of the present invention. Similarly, reacting the hydroxy compound (XIII) with an activated acyl group L—C(O)R$^{11}$ (where L is a group that activates carboxylic acid coupling reactions such as halo, imidazole, or mixed anhydride) gives an ester compound (XV) of the present invention.

One method to obtain the sulfur analogs of the present invention is shown in Scheme 3. A 4-thiocyanato phenol (XVI) is reacted with N-chlorosulfonyl isocyanate at elevated temperatures, and quenched with water to give the sulfamate (XVII). This is then coupled with the phenyl acetic acid analog (III) using standard coupling techniques (e.g., DCC, CDI, acid chloride, or mixed anhydride) to give the thiocyanato compound of the present invention (XVIII). Hydrolysis of the thiocyanato group gives the thiol (XIX) which can be functionalized to give the compounds of the present invention. For example, alkylating with an activated alkyl group X—(CH$_2$)$_n$NR$^9$R$^{10}$ (where X is halo, triflate, or other similar leaving groups known to those skilled in the art, and n, R$^9$, and R$^{10}$ have the meanings defined in the scope of this patent) gives a thioether compound (XX) of the present invention. Oxidation of the thioether (XX) gives the sulfoxide (XXI, m=1) or sulfone (XXI, m=2). The thiocyanato compound (XVIII) can also be oxidized to give the sulfonic acid compound (XXII) which can be further functionalized by coupling with an activated alkyl group (X alkyl) to give the sulfonate ester (XXIII) or an amine (HNR$^9$R$^{10}$) to give a sulfonamide (VXXIV).

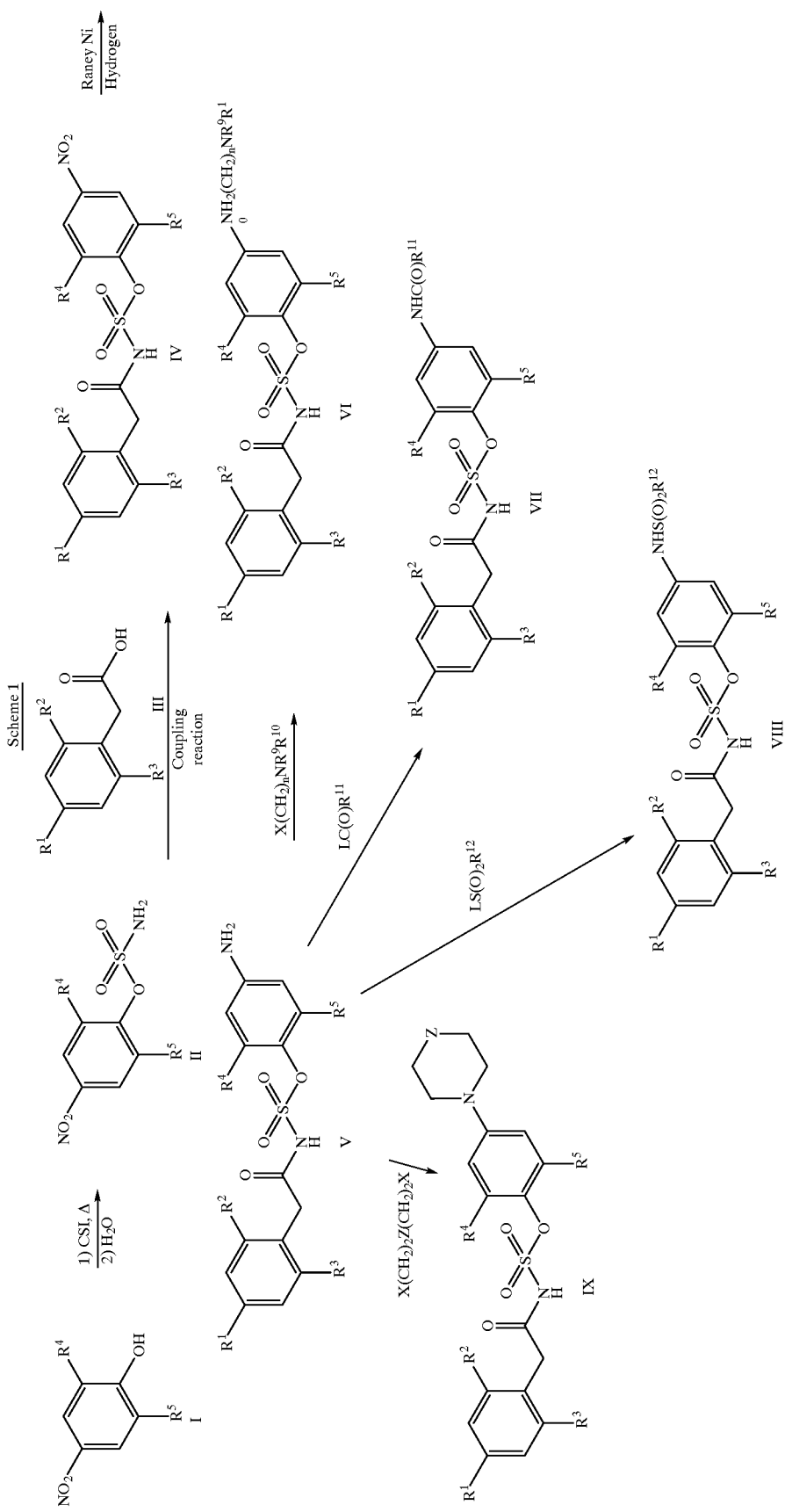

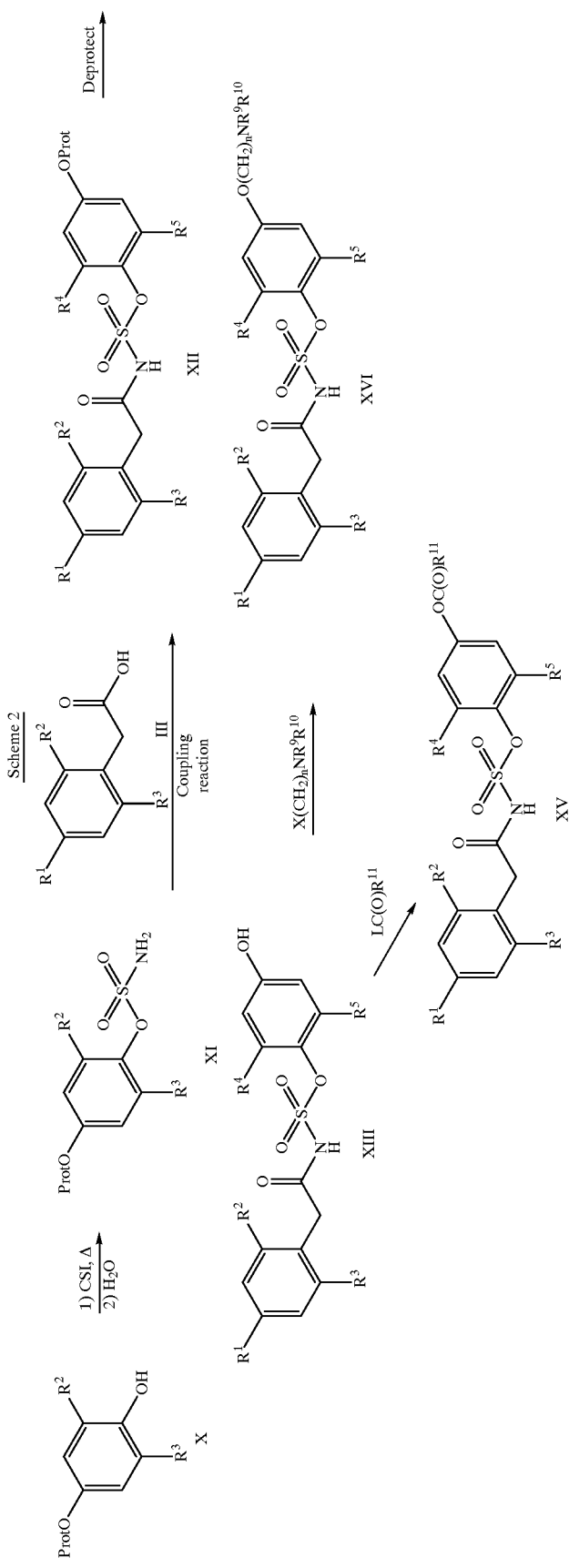

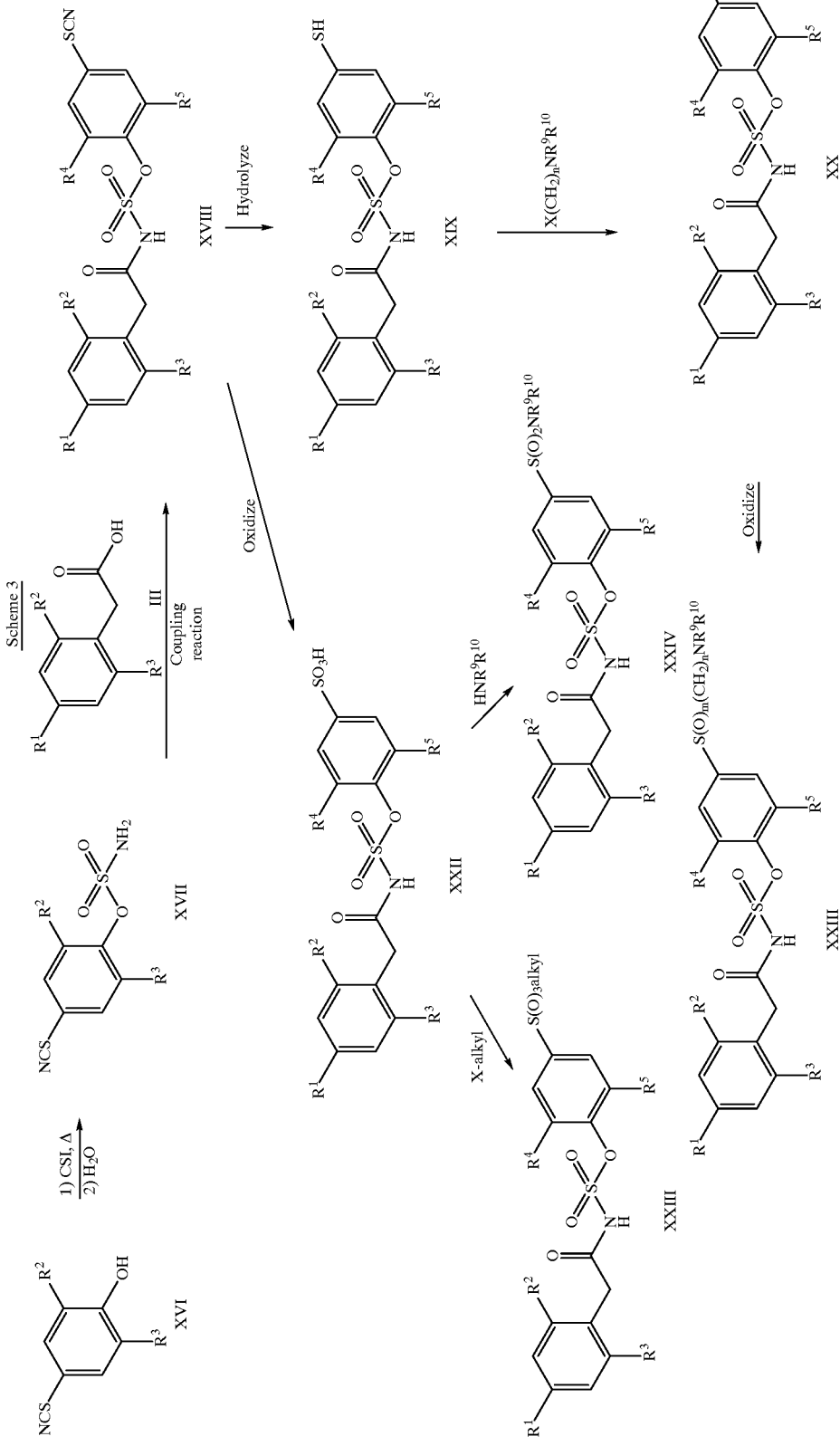

Synthesis of 2,6-bis(1-methylethyl)-4-nitrophenyl sulfamate

N-Chlorosulfonyl isocyanate (7.2 mL, 82.6 mmol) was added slowly to a warm solution of 2,6-bis(1-methylethyl)-4-nitrophenol (17.57 g, 78.7 mmol) in 400 mL toluene. The resulting solution was heated to reflux for 6 hours and then cooled to room temperature and concentrated to give a brown oil. Quenched with 200 g ice and extracted with 4×500 mL dichloromethane. The organic solution was dried over $MgSO_4$, filtered, and concentrated to give a tan solid. Recrystallization from dichloromethane gave 14.18 g (60%) of the title compound as an off-white solid; mp 163–167° C.

Synthesis of [(2,4,6-Triisopropyl-phenyl)-acetyl]-sulfamic acid 2,6-diisopropyl-4-nitro-phenyl ester Oxalyl chloride (0.52 mL, 5.9 mmol) was added dropwise to a solution of 2,4,6-tris(1-methylethyl)-phenyl acetic acid in 150 mL toluene with four drops N,N-dimethylformamide added as a catalyst. The resulting solution was stirred for 4 hours at room temperature and concentrated in vacuo. The residue was redissolved in 200 mL dichloromethane with 2,6-bis(1-methylethyl)-4-nitrophenyl sulfamate (1.50 g, 4.9 mmol) and excess (3 mL) triethylamine and stirred for 16 hours. The reaction was washed with 1 M HCl, dried over $MgSO_4$, filtered, and concentrated to give an oily solid. Recrystallization from hexanes gave 2.37 g (87%) of the title compound as a white solid; mp 85–89° C.

Synthesis of [(2,4,6-Triisopropyl-phenyl)-acetyl]-sulfamic acid 4-amino-2,6-diisopropyl-phenyl ester 22.0 g of [(2,4,6-Triisopropyl-phenyl)-acetyl]-sulfamic acid 2,6-diisopropyl-4-nitro-phenyl ester and 6 g of Raney nickel were mixed in 110 mL tetrahydrofuran under 50 psi of hydrogen. After 21 hours, the reaction was filtered and concentrated to give an orange oil which was dissolved in ethyl acetate, filtered through a pad of silica, and concentrated to give an oily solid. Recrystallization from 53 diethyl ether/hexanes gave 18.60 g (89%) of the title compound as a cream colored solid; mp 153–155° C.

Synthesis of 2,6-Bis(1-methylethyl)-4-cyanophenyl sulfamate

Step (a)

2,6-Bis(1-methylethyl)-4-(N-(1-methylethyl)carboxamide)phenol

4-Cyanophenol (40.0 g, 336 mmol) was added in portions to a mixture of isopropanol (103 mL, 1.34 mol) and 80% sulfuric acid (300 mL) at 70° C. Heated for 20 hours then cooled to room temperature and quenched with ice. The resulting suspension was extracted with ethyl acetate. The ethyl acetate layer was dried over magnesium sulfate, filtered, and concentrated to give a green oil. Chromatography on silica gel (30% ethyl acetate/hexanes) gave 46.0 g of 2,6-bis(1-methylethyl)-4-(N-(1-methylethyl)carboxamide)phenol as a white solid; mp 165–167° C.

Step (b)

2,6-Bis(1-methylethyl)-4-cyanophenyl sulfamate

N-Chlorosulfonyl isocyanate (3.5 mL, 39.9 mmol) was added slowly to a warm solution of 2,6-bis(1-methylethyl)-4-(N-(1-methylethyl)carboxamide)phenol (5.0 g, 19.0 mmol) in 300 mL toluene. The resulting solution was heated to reflux for 6 hours and then cooled to room temperature and concentrated to give a brown oil. Quenched with 200 g ice and extracted with ethyl acetate. The organic solution was dried over magnesium sulfate, filtered, and concentrated to give a tan solid. Chromatography on silica gel (20% ethyl acetate/hexanes) gave 1.20 g of the title compound as an off-white solid.

Synthesis of 2,6-Bis(1-methylethyl)-4-formylphenyl sulfamate

N-Chlorosulfonyl isocyanate (21.6 mL, 248 mmol) was added slowly to a warm solution of 3,5-diisopropyl-4-hydroxy-benzaldehyde (24.4 g, 118 mmol) in 500 mL toluene. The resulting solution was heated to reflux for 4 hours and then cooled to room temperature and concentrated to give a brown oil. Quenched with 200 g ice and extracted with ethyl acetate. The organic solution was dried over magnesium sulfate, filtered, and concentrated to give a tan solid. Chromatography on silica gel (20% ethyl acetate/hexanes) gave 11.15 g of the title compound as an off-white solid.

Synthesis of 3,5-Diisopropyl-4-{[(2,4,6-triisopropyl-phenyl)-acetyl]sulfamoyloxy}-benzoic acid methyl ester Step (a)

3,5-Bis(1-methylethyl)-4-(sulfamoyloxy)benzoic acid methyl ester

N-Chlorosulfonyl isocyanate (2.12 mL, 24.3 mmol) was added slowly to a warm solution of 3,5-diisopropyl-4-hydroxy-benzoic acid methyl ester (5.47 g, 23.1 mmol) in 300 mL toluene. The resulting solution was heated to reflux for 6 hours and then cooled to room temperature and concentrated to give a brown oil. Quenched with 200 g ice and extracted with ethyl acetate. The organic solution was dried over magnesium sulfate, filtered, and concentrated to give a tan solid. Chromatography on silica gel (20% ethyl acetate/hexanes) gave 3.58 g of the title compound as an off-white solid.

Step (b)

3,5-Diisopropyl-4-{[(2,4,6-triisopropyl-phenyl)-acetyl]sulfamoyloxy}-benzoic acid methyl ester Oxalyl chloride (1.12 mL, 12.8 mmol) was added dropwise to a solution of 2,4,6-triisopropylphenyl acetic acid (3.05 g, 11.6 mmol) in 150 mL toluene with 4 drops of N,N-dimethylformamide as a catalyst. The resulting solution was stirred overnight and then concentrated in vacuo. The residue was re-dissolved in 150 mL dichloromethane. 3,5-Bis(1-methylethyl)-4-(sulfamoyloxy)benzoic acid methyl ester (3.48 g, 11.6 mmol) and triethylamine (4.0 mL) were added and the resulting mixture was stirred for 2 hours. Washed with 1 M HCl, dried the organic layer over magnesium sulfate, filtered, and concentrated to give an off-white foam. Recrystallized (hexanes) to give 5.21 g of the title compound as a white solid; mp 144–146° C.

Synthesis of 6-(3,5-Diisopropyl-4-sulfamoyloxy-phenyl)-hexanoic acid ethyl ester Step (a)

6-(4-Hydroxy-3,5-diisopropyl-phenyl)-6-oxo-hexanoic acid ethyl ester

Monomethyl adipate (61 g, 350 mmol) was treated with excess oxalyl chloride in tetrahydrofuran. The mixture was concentrated, and the resulting acid chloride was mixed with 2,6-Diisopropyl phenol (57 g, 350 mmol) at 0° C. Aluminum chloride (93 g, 700 mmol) and a catalytic amount of 1,2-dichloroethane were added in portions, and the mixture was allowed to warm to room temperature and stirred overnight. The reaction was quenched with 1 M HCl and extracted with ethyl acetate. Concentrated in vacuo and chromatographed the residue to give the expected product.
Step (b)

6-(4-Hydroxy-3,5-diisopropyl-phenyl)-hexanoic acid ethyl ester

Boron trifluoride diethyl etherate (4.8 mL, 39 mmol) was added to a mixture of 6-(4-hydroxy-3,5-diisopropyl-phenyl)-6-oxo-hexanoic acid ethyl ester (13.19 g, 39.4 mmol) and ethanedithiol (3.5 mL, 39.3 mmol) in dichloromethane (100 mL), and the resulting deep red mixture was stirred overnight at room temperature. An additional amount of boron trifluoride diethyl etherate (1.2 mL, 10 mmol) was added, and the reaction mixture was stirred an additional 4 hours at room temperature. The reaction mixture was washed with saturated aqueous sodium bicarbonate solution, and the organic solution was dried over magnesium sulfate, filtered, and concentrated to an orange oil. The oil was chromatographed on silica gel (70–230 mesh) using 19:1, then 9:1, then 83:17 hexanes/ethyl acetate, v/v, as eluant. A mixture of this dithioketal (3.65 g, 8.9 mmol), Raney nickel (41 g of a slurry in water), and ethanol (250 mL) is heated to 50° C. for 2.5 hours under nitrogen. No starting material remained by tlc. The ethanol was decanted from the nickel and the nickel washed and decanted twice with ethanol. The combined ethanol solutions were passed through celite, the ethanol evaporated, and the residue chromatographed on silica gel (70 230 mesh) using 4:1, hexanes/ethyl acetate as eluant. The product was obtained as a yellow oil in two portions, 2.95 g. CI Mass Spectrum: $[M+H^+]^+=320$.
Step (c)

6-(3,5-Diisopropyl-4-sulfamoyloxy-phenyl)-hexanoic acid ethyl ester

Sodium hydride (0.257 g, 6.4 mmol) was added to 6-(4-hydroxy-3,5-diisopropyl-phenyl)-hexanoic acid ethyl ester (1.46 g, 5.0 mmol) in dimethylformamide (20 mL) at 0° C. over about 3 minutes. The cooling bath was removed, and the mixture was stirred at room temperature for 10 minutes. The reaction mixture was cooled to zero degrees and sulfamoyl chloride (1.18 g, 10.3 mmol) was added over ~3 minutes. The reaction mixture was stirred 1.5 hours at zero degrees and was quenched by adding saturated aqueous sodium bicarbonate solution. The mixture is diluted with diethyl ether (300 mL) and water (100 mL). The organic layer is washed with water (3×100 mL), brine, dried over magnesium sulfate, filtered, and concentrated to an oil. The oil is chromatographed on silica gel using 4:1 hexanes/ethyl acetate as eluant. The title compound is obtained as a light yellow oil, 1.29 g. CI Mass Spectrum: $[M+H^+]^+=400$.

EXAMPLE 1

Synthesis of (S)-[5-tert-Butoxycarbonylamino-5-(3,5-diisopropyl-4-{[(2,4,6-triisopropyl-phenyl)-acetyl]-sulfamoyloxy}-phenylcarbanoyl)-pentyl]-carbamic acid tert-butyl ester N,N-Dicyclohexylcarbodiimide (0.63 g, 3.0 mmol) was added to a solution of [(2,4,6-Triisopropyl-phenyl)-acetyl]-sulfamic acid 4-amino-2,6-diisopropyl-phenyl ester (1.5 g, 2.9 mmol) and bis-N,N'-(t-butoxycarbonyl)-(S)-lysine (1.1 g, 2.9 mmol) in 100 mL of dichloromethane at –15° C. under an atmosphere of nitrogen. The resulting mixture was allowed to warm to room temperature and stirred for 16 hours. The reaction was filtered, concentrated, and chromatographed on silica gel to give an oily solid. Recrystallization from 5% diethyl ether/hexanes gave 1.61 g (66%) of the title compound as a white solid; mp 167–171° C.

EXAMPLE 2

Synthesis of (S)-[(2,4,6-Triisopropyl-phenyl)-acetyl]-sulfamic acid 4-(2,6-diamino-hexanoylamino)-2,6-diisopropyl-phenyl ester dihydrochloride HCl (g) was bubbled through a solution of (S)-[5-tert-butoxycarbonylamino-5-(3,5-diisopropyl-4-{[(2,4,6-triisopropyl-phenyl)-acetyl]sulfamoyloxy}-phenylcarbamoyl)-pentyl]-carbamic acid tert-butyl ester (1.08 g, 1.3 mmol) in 150 mL methanol for 30 minutes. The reaction was concentrated, and the resulting foam was triturated with 5% dichloromethane/hexanes to give 0.88 g (96%) of the title compound as a tan solid; mp 172–179° C.

EXAMPLE 3

Synthesis of [(3,5-Diisopropyl-4-{[(2,4,6-triisopropyl)-phenyl)-acetyl]sulfamoyloxy}-phenylcarbamoyl)-methyl]-carbamic acid tert-butyl ester When in the procedure of Example 1, bis-N,N'-(t-butoxycarbonyl)-(S)-lysine is replaced with N-(t-butoxycarbonyl)-glycine, the title compound is obtained; mp 177–188° C.

EXAMPLE 4

Synthesis of [(2,4,6-Triisopropyl-phenyl)-acetyl]-sulfamic acid 4-(2-amino-acetylamino)-2,6-diisopropyl-phenyl ester When in the procedure of Example 1, bis-N,N'-(t-butoxycarbonyl)-(S)-lysine is replaced with N-(9-fluorenylmethyoxycarbonyl)-glycine, and the crude product is stirred in 20% piperidine/N,N-dimethyl-formamide for 0.5 hours and purified by chromatography, the title compound is obtained.

EXAMPLE 5

Synthesis of [(2,4,6-Triisopropyl-phenyl)-acetyl]-sulfamic acid 4-(2-t-butoxycarbonylamino-4-methylsulfanyl-butyrylamino)-2,6-diisopropyl-phenyl ester When in the procedure of Example 1, bis-N,N'-(t-butoxycarbonyl)-(S)-lysine is replaced with N-(t-butoxycarbonyl)-methionine, the title compound is obtained.

EXAMPLE 6

Synthesis of [(2,4,6-Triisopropyl-phenyl)-acetyl]-sulfamic acid 4-(2-amino-4-methylsulfanyl-butyrylamino)-2,6-diisopropyl-phenyl ester trifluoroacetate (2,4,6-Triisopropyl-phenyl)-acetyl]-sulfamic acid 4-(2-t-butoxycarbonylamino-4-methylsulfanyl-butyrylamino)-2,6-diisopropyl-phenyl ester (0.2 g, 0.3 mmol) was dissolved in 30 mL 50% trifluroacetic acid/dichloromethane and stirred for 15 minutes. The title compound was isolated as an off-white solid.

EXAMPLE 7

Synthesis of 3-[3-(3,5-Diisopropyl-4-{[(2,4,6-triisopropyl)-phenyl)-acetyl]sulfamoyloxy}-phenyl)-ureido]-propionic acid ethyl ester Ethyl 3-isocyanatopropionate (0.29 g, 2.0 mmol) was added to a solution of [(2,4,6-triisopropyl-phenyl)-acetyl]-sulfamic acid 4-amino-2,6-diisopropyl-phenyl ester (1.0 g, 1.9 mmol) in 50 mL dichloromethane under a dry air atmosphere. Stirred for 6 hours, concentrated in vacuo, and triturated the residue with 5% ethyl acetate in hexanes to give 1.04 g of the title compound as an off-white solid, mp 182–185° C.

EXAMPLE 8

Synthesis of 3-[3-(3,5-Diisopropyl-4-{[(2,4,6-triisopropyl)-phenyl)-acetyl]sulfamoyloxy}-phenyl)-ureido]-propionic acid 3-[3-(3,5-Disopropyl-4-{[(2,4,6-triisopropyl-phenyl)-acetyl]sulfamoyloxy}-phenyl)-ureido]-propionic acid ethyl ester (0.54 g, 0.84 mmol) was suspended in 50 mL of 70% ethanol and 1.7 mL of 1M NaOH was added. The resulting mixture was stirred overnight, washed with diethyl ether, acidified with concentrated HCl, and extracted with dichloromethane. The organics were dried over magnesium sulfate, filtered, and concentrated to leave an oily solid which was triturated with 50% ethyl acetate in hexanes to give the title compound as a white solid, mp 179–181° C.

EXAMPLE 9

Synthesis of [(2,4,6-Triisopropyl-phenyl)-acetyl]-sulfamic acid 4-[(2-amino-3-(1H-indol-3-yl)-propionylamino]-2,6-diisopropyl-phenyl ester When in the procedure of Example 1, bis-N,N'-(t-butoxycarbonyl)-(S)-lysine is replaced with N-(9-fluorenylmethyoxycarbonyl)-tryptophan, and the crude product is stirred in 20% piperidine/N,N-dimethylformamide for 0.5 hours and purified by chromatography, the title compound is obtained.

EXAMPLE 10

Synthesis of [(2,4,6-Triisopropyl-phenyl)-acetyl]-sulfamic acid 4-(5-amino-pentanoylamino)-2,6-diisopropyl-phenyl ester trifluoroacetate(1:1) (salt)

When in the procedure of Example 1, bis-N,N'-(t-butoxycarbonyl)-(S)-lysine is replaced with N-(t-butoxycarbonyl)-5-aminopentanoic acid, and the t-butoxycarbonyl protecting group is removed by stirring for 15 minutes in a 50% trifluoroacetic acid solution in dichloromethane, the title compound is obtained.

EXAMPLE 11

Synthesis of (D)-[(2,4,6-Triisopropyl-phenyl)-acetyl]-sulfamic acid 4-(2-amino-propionylamino)-2,6-diisopropyl-phenyl ester trifluoroacetate(1:1) (salt)

When in the procedure of Example 1, bis-N,N'-(t-butoxycarbonyl)-(S)-lysine is replaced with N-(t-butoxycarbonyl)-(D)-alanine, and the t-butoxycarbonyl protecting group is removed by stirring for 15 minutes in a 50% trifluoroacetic acid solution in dichloromethane, the title compound is obtained.

EXAMPLE 12

Synthesis of (L)-[(2,4,6-Triisopropyl-phenyl)-acetyl]-sulfamic acid 4-(2-amino-propionylamino)-2,6-diisopropyl-phenyl ester When in the procedure of Example 1, bis-N,N'-(t-butoxycarbonyl)-(S)-lysine is replaced with N-(9-fluorenylmethyoxycarbonyl)-(L)-alanine, and the crude product is stirred in 20% piperidine/N,N-dimethylformamide for 0.5 hours and purified by chromatography, the title compound is obtained.

EXAMPLE 13

Synthesis of [(2,4,6-Triisopropyl-phenyl)-acetyl]-sulfamic acid 4-(2-amino-2-methyl-propionylamino)-2,6-diisopropyl-phenyl ester When in the procedure of Example 1, bis-N,N'-(t-butoxycarbonyl)-(S)-lysine is replaced with N-(9-fluorenylmethyoxycarbonyl)-(alpha-methyl)alanine, and the crude product is stirred in 20% piperidine/N,N-dimethylformamide for 0.5 hours and purified by chromatography, the title compound is obtained.

EXAMPLE 14

Synthesis of [(2,4,6-Triisopropyl-phenyl)-acetyl]-sulfamic acid 4-(3-dimethylamino-propoxy)-2,6-diisopropyl-phenyl ester Step (a)

2,6-Bis(1-methylethyl)-1,4-dihydroquinone

A solution of potassium persulfate (30.33 g, 112 mmol) in 250 mL water was added dropwise over 1 hour to a solution of 2,6-bis(1-methylethyl)phenol (20.0 g, 112 mmol) in 250 mL 10% aqueous sodium hydroxide at 0° C. The resulting dark mixture was warmed to room temperature and stirred overnight. Neutralized to pH 7.0 with concentrated HCl and washed with diethyl ether. The aqueous layer was acidified with additional concentrated HCl and heated on a steam bath for 0.5 hour. Cooled to room temperature and extracted with diethyl ether. The organic layer was dried over magnesium sulfate, filtered, and concentrated to give 10.5 g of 2,6-bis (1-methylethyl)-1,4-dihydroquinone as a dark oil which solidified upon standing.

Step (b)

4-(tert-butyl-dimethyl-silanyloxy)-2,6-diisopropylphenol 2,6-Bis(1-methylethyl)-1,4-dihydroquinone (21.32 g, 109 mmol) and tert-butyl-dimethyl-silyl chloride (18.2 g, 121 mmol) were mixed in 300 mL dichloromethane at room temperature. Triethylamine (18.4 mL, 133 mmol) was added, and the resulting mixture was stirred for 3 days. The reaction was washed with 1M HCl, and the organic layer was dried over magnesium sulfate, filtered, and concentrated to give 20.24 g of 4-(tert-butyl-dimethyl-silanyloxy)-2,6-diisopropyl-phenol as an orange oil.

Step (c)

4-(tert-butyl-dimethyl-silanyloxy)-2,6-diisopropylphenol sulfamate

N-Chlorosulfonyl isocyanate (3.43 mL, 39.4 mmol) was added to a warm solution of 4-(tert-butyl-dimethylsilanyloxy)-2,6-diisopropylphenol (11.59 g, 37.6 mmol) in 400 mL toluene. The resulting solution was heated to reflux for 6 hours and then cooled to room temperature and stirred overnight. The reaction was concentrated in vacuo, and the residue was quenched with ice water and extracted with dichloromethane. The organic layer was dried over magnesium sulfate, filtered, and concentrated to give an orange oil. Chromatography on silica gel gave 6.06 g of 4-(tert-butyl-dimethyl-silanyloxy)-2,6-diisopropylphenyl sulfamate as an orange oil.

Step (d)

[(2,4,6-Triisopropyl-phenyl)-acetyl]-sulfamic acid 4-(tert-butyl-dimethyl-silanylloxy)-2,6-diisopropyl-phenyl ester Oxalyl chloride (2.45 mL, 28 mmol) was added dropwise to a solution of 2,4,6-triisopropylphenyl acetic acid (5.66 g, 21.6 mmol) in 150 mL toluene with 4 drops of N,N-dimethylformamide as a catalyst. The resulting solution was stirred for 6 hours and then concentrated in vacuo. The residue was redissolved in 150 mL dichloromethane. 4-(Tert-butyl-dimethyl-silanyloxy)-2,6-diisopropylphenyl sulfamate (8.36 g, 21.6 mmol) and triethylamine (7.5 mL, 54 mmol) were added, and the resulting mixture was stirred overnight. Washed with 1M HCl, dried the organic layer over magnesium sulfate, filtered, and concentrated to give 9.86 g of [(2,4,6-triisopropyl-phenyl)-acetyl]-sulfamic acid 4-(tert-butyl-dimethyl-silanyloxy)-2,6-diisopropyl-phenyl ester.

Step (e)

[(2,4,6-Triisopropyl-phenyl)-acetyl]-sulfamic acid 4-hydroxy-2,6-diisopropyl-phenyl ester A solution of 15 mL concentrated HF in 150 mL acetonitrile was added dropwise to a solution of [(2,4,6-triisopropyl-phenyl)-acetyl]-sulfamic acid 4-(tert-butyl-dimethyl-silanyloxy)-2,6-diisopropyl-phenyl ester (9.71 g, 15.4 mmol) in 400 mL acetonitrile at room temperature under a nitrogen atmosphere. Stirred for 16 hours and then concentrated in vacuo. The residue was partitioned between water and dichloromethane. The organic layer was dried over magnesium sulfate, filtered, and concentrated to give an oily solid. Trituration with hexanes gave 7.24 g of [(2,4,6-triisopropyl-phenyl)-acetyl]-sulfamic acid 4-hydroxy-2,6-diisopropyl-phenyl ester as a white solid; mp 182–183° C.

Step (f)

[(2,4,6-Triisopropyl-phenyl)-acetyl]-sulfamic acid 4-(3-dimethylamino-propoxy)-2,6-diisopropyl-phenyl ester Solid sodium hydride (0.16 g, 4 mmol) was added to a solution of [(2,4,6-triisopropyl-phenyl)-acetyl]-sulfamic acid 4-hydroxy-2,6-diisopropyl-phenyl ester (1.0 g, 1.9 mmol) in 50 mL of N,N-dimethylformamide. The resulting mixture was stirred for 1 hour before a mixture of triethylamine (1.08 mL, 7.8 mmol) and 3-dimethylaminopropylchloride hydrochloride (1.22 g, 3.9 mmol) in 75 mL tetrahydrofuran was added dropwise. The resulting mixture was stirred for 16 hours and then concentrated in vacuo. The residue was partitioned between saturated citric acid and dichloromethane. The organic layer was dried over magnesium sulfate, filtered, and concentrated to give an oily solid. Trituration with a small amount of diethyl ether gave 0.36 g of [(2,4,6-Triisopropyl-phenyl)-acetyl]-sulfamic acid 4-(3-dimethylamino-propoxy)-2,6-diisopropyl-phenyl ester as a white foam.

EXAMPLE 15

Synthesis of [(2,4,6-Triisopropyl-phenyl)-acetyl]-sulfamic acid 4-(3-dimethylamino-propoxy)-2,6-diisopropyl-phenyl ester hydrochloride salt

[(2,4,6-Triisopropyl-phenyl)-acetyl]-sulfamic acid 4-(3-dimethylamino-propoxy)-2,6-diisopropyl-phenyl ester (0.2 g) was suspended in 50 mL of diethyl ether and HCl(g) was bubbled through the solution for 15 minutes. The solution was concentrated in vacuo to give [(2,4,6-triisopropyl-phenyl)-acetyl]-sulfamic acid-4-(3-dimethylamino-propoxy)-2,6-diisopropyl-phenyl ester hydrochloride salt as a white foam.

EXAMPLE 16

Synthesis of [(2,4,6-Triisopropyl-phenyl)-acetyl]-sulfamic acid 4-(3-amino-propoxy)-2,6-diisopropyl-phenyl ester hydrochloride salt Step (a)

[(2,4,6-Triisopropyl-phenyl)-acetyl]-sulfamic acid 4-(3-tert-butoxycarbonylamino-propoxy)-2,6-diisopropyl-phenyl ester This compound was prepared in the same manner as Example 14, except that 3-tert-butoxycarbonylamino-propyl alcohol was used in place of the triethylamine and 3-dimethylaminopropylchloride hydrochloride mixture.

Step (b)

[(2,4,6-Triisopropyl-phenyl)-acetyl]-sulfamic acid 4-(3-amino-propoxy)-2,6-diisopropyl-phenyl ester hydrochloride salt HCl(g) was bubbled through a solution of [(2,4,6-triisopropyl-phenyl)-acetyl]-sulfamic acid 4-(3-tert-butoxycarbonylamino-propoxy)-2,6-diisopropyl-phenyl ester in 150 mL methanol for 15 minutes. Concentrated in vacuo and triturated the residue with 500 diethyl ether in hexanes to give [(2,4,6-triisopropyl-phenyl)-acetyl]-sulfamic acid 4-(3-amino-propoxy)-2,6-diisopropyl-phenyl ester hydrochloride salt as an off-white solid.

EXAMPLE 17

Synthesis of [(2,4,6-Triisopropyl-phenyl)-acetyl]-sulfamic acid 2,6-diisopropyl-4-thiocyanato-phenyl ester Step (a)

Sulfamic acid 2,6-diisopropyl-4-thiocyanato-phenyl ester

N-Chlorosulfonyl isocyanate (1.02 mL, 11.7 mmol) was added to a warm solution of 2,6-diisopropyl-4-thiocyanato-phenol (2.5 g, 10.6 mmol) in 150 mL toluene. The resulting solution was heated to reflux for 6 hours and then cooled to room temperature and stirred overnight. The reaction was concentrated in vacuo and the residue was quenched with ice water and extracted with dichloromethane. The organic layer was dried over magnesium sulfate, filtered, and concentrated to give 1.75 g of sulfamic acid 2,6-diisopropyl-4-thiocyanato-phenyl ester as a white solid.

Step (b)

[(2,4,6-Triisopropyl-phenyl)-acetyl]-sulfamic acid 2,6-diisopropyl-4-thiocyanato-phenyl ester Oxalyl chloride (0.6 mL, 6.9 mmol) was added dropwise to a solution of 2,4,6-triisopropylphenyl acetic acid (1.52 g, 5.8 mmol) in 150 mL toluene with 4 drops of N,N-dimethylformamide as a catalyst. The resulting solution was stirred overnight and then concentrated in vacuo. The residue was redissolved in 150 mL dichloromethane. Sulfamic acid 2,6-diisopropyl-4-thiocyanato-phenyl ester (1.70 g, 5.8 mmol) and triethylamine (2.0 mL) were added, and the resulting mixture was stirred for 2 hours. Washed with 1M HCl, dried the organic layer over magnesium sulfate, filtered, and concentrated to give 2.24 g of [(2,4,6-triisopropyl-phenyl)-acetyl]-sulfamic acid 2,6-diisopropyl-4-thiocyanato-phenyl ester as a white solid; mp 164–165° C.

EXAMPLE 18

Synthesis of [(2,4,6-Triisopropyl-phenyl)-acetyl]-sulfamic acid 4-cyano-2,6-diisopropyl-phenyl ester Oxalyl chloride (0.48 mL, 5.5 mmol) was added dropwise to a solution of 2,4,6-triisopropylphenyl acetic acid (1.21 g, 4.6 mmol) in 100 mL toluene with 4 drops of N,N-dimethylformamide as a catalyst. The resulting solution was stirred overnight and then concentrated in vacuo. The residue was re-dissolved in 150 mL dichloromethane. 2,6-Bis(l-methylethyl)-4-cyanophenyl sulfamate (1.30 g, 4.6 mmol) and triethylamine (1.6 mL) were added, and the resulting mixture was stirred for 6 hours. Washed with 1 M HCl, dried the organic layer over magnesium sulfate, filtered, and concentrated to give an oily solid. Chromatography on silica gel (20% ethyl acetate/hexanes) gave 1.11 g of the title compound as a white solid; mp 79–84° C.

EXAMPLE 19

Synthesis of [(2,4,6-Triisopropyl-phenyl)-acetyl]-sulfamic acid 4-[(2-amino-acetylamino)-methyl]-2,6-diisopropyl-phenyl ester Step (a)

[(2,4,6-Triisopropyl-phenyl)-acetyl]-sulfamic acid 4-(aminomethylene)-2,6-diisopropyl-phenyl ester

[(2,4,6-Triisopropyl-phenyl)-acetyl]-sulfamic acid 4-cyano-2,6-diisopropyl-phenyl ester (5.15 g, 9.8 mmol) was dissolved in 100 mL of methanolic ammonia and 2.0 g of Raney-nickel was added. The resulting mixture was stirred under 50 psi of hydrogen at room temperature for 20 hours. Filtered and concentrated the residue to give a dark solid. Suspended in diethyl ether and acidified with HCl gas. Concentrated in vacuo and neutralized the residue with saturated aqueous sodium bicarbonate. The resulting white suspension was used without further purification.

Step (b)

[(2,4,6-Triisopropyl-phenyl)-acetyl]-sulfamic acid 4-[(2-amino-acetylamino)-methyl]-2,6-diisopropyl-phenyl ester When in the procedure of Example 1, bis-N,N'-(t-butoxycarbonyl)-(S)-lysine is replaced with N-(9-fluorenylmethyoxycarbonyl)-glycine, [(2,4,6-triisopropyl-phenyl)-acetyl]-sulfamic acid 4-amino-2,6-diisopropyl-phenyl ester is replaced by [(2,4,6-triisopropyl-phenyl)-acetyl]-sulfamic acid 4-(aminomethylene)-2,6-diisopropyl-phenyl ester, and the crude product is stirred in 20% piperidine/N,N-dimethylformamide for 0.5 hours followed by trituration with hexanes, the title compound is obtained; mp 193–195° C.

EXAMPLE 20

Synthesis of [(2,4,6-Triisopropyl-phenyl)-acetyl]-sulfamic acid 4-formyl-2,6-diisopropyl-phenyl ester When in the procedure of Example 8, 2,6-Bis(1-methylethyl 2)-4-cyanophenyl sulfamate is replaced with 2,6-bis(1-methylethyl)-4-formylphenyl sulfamate, the title compound is obtained; mp 71–76° C.

EXAMPLE 21

Synthesis of [(2,4,6-Triisopropyl-phenyl)-acetyl]-sulfamic acid 4-(2-cyano-vinyl)-2,6-diisopropyl-phenyl ester Diethylcyanomethyl phosphonate (1.49 mL, 9.2 mmol) was added dropwise to a suspension of sodium hydride (0.37 g, 9.2 mmol) in 20 mL tetrahydrofuran at 0° C. After 15 minutes, the reaction was cooled to −78° C. and a solution of [(2,4,6-triisopropyl-phenyl)-acetyl]-sulfamic acid 4-formyl-2,6-diisopropyl-phenyl ester (2.32 g, 4.4 mmol) in 75 mL tetrahydrofuran was added dropwise. The reaction was allowed to warm to room temperature overnight and then concentrated in vacuo and partitioned the residue between 1 M HCl and dichloromethane. The organic layer was dried over magnesium sulfate, filtered, and concentrated to give an oily solid. Chromatography on silica gel (20% ethyl acetate/hexanes) gave 1.16 g of the title compound as a white solid; mp 157–160° C.

EXAMPLE 22

Synthesis of [(2,4,6-Triisopropyl-phenyl)-acetyl]-sulfamic acid 4-(benzylamino-methyl)-2,6-diisopropyl-phenyl ester mono hydrochloride

[(2,4,6-Triisopropyl-phenyl)-acetyl]-sulfamic acid 4-formyl-2,6-diisopropyl-phenyl ester (1.0 g, 1.9 mmol), benzylamine (0.21 mL, 1.9 mmol), and sodium triacetoxyborohydride (0.56 g, 2.6 mmol) were mixed in 100 mL of dichloromethane under a dry air atmosphere for 16 hours. Quenched by adding saturated sodium bicarbonate (50 mL). The resulting white solid was collected by filtration and resuspended in diethyl ether. HCl gas was bubbled through for 30 minutes, and the resulting solution was concentrated in vacuo to give the title compound as a white solid; mp 179–183° C.

EXAMPLE 23

Synthesis of [(2,4,6-Triisopropyl-phenyl)-acetyl]-sulfamic acid 2,6-diisopropyl-4-(4-methyl-piperazin-1-ylmethyl)-phenyl ester, dihydrochloride When in the procedure of Example 22, benzylamine is replaced with 1-methyl piperazine, the title compound is obtained; mp 166–172° C.

EXAMPLE 24

Synthesis of [(2,4,6-Triisopropyl-phenyl)-acetyl]-sulfamic acid 4-carbamoyl-2,6-diisopropyl-phenyl ester 3,5-Diisopropyl-4-{[(2,4,6-triisopropyl-phenyl)-acetyl] sulfamoyloxy}-benzoic acid methyl ester (3.13 g, 5.6 mmol) was dissolved in a 3:1 methanol/1 M NaOH solution and stirred for 16 hours, concentrated in vacuo, and partitioned the residue between water and diethyl ether. The aqueous layer was acidified with concentrated HCl and extracted with ethyl acetate to give 2.85 g of the carboxylic acid as an off-white solid. Oxalyl chloride (0.16 mL, 1.8 mmol) was added dropwise to a suspension of the carboxylic acid (0.9 g, 1.65 mmol) in 50 mL toluene with 4 drops of N,N-dimethylformamide as a catalyst. The resulting solution was stirred for 2 hours, and then concentrated in vacuo. The residue was re-dissolved in 30 mL of methanolic ammonia, and the resulting mixture was stirred overnight. Concentrated in vacuo and partitioned between 1 M HCl and ethyl acetate. Dried the organic layer over magnesium sulfate, filtered, and concentrated to give a white solid. Chromatography on silica gel (20% ethyl acetate/hexanes) gave 0.17 g of the title compound as a white foam.

EXAMPLE 25

Synthesis of [(2,4,6-Triisopropyl-phenyl)-acetyl]-sulfamic acid 4-hydroxymethyl-2,6-diisopropyl-phenyl ester 3.9 mL of a 1 M solution of diisobutyl aluminum hydride in dichloromethane was added to a solution of 3,5-Diisopropyl-4-{[(2,4,6-triisopropyl-phenyl)-acetyl]sulfamoyloxy}-benzoic acid methyl ester (1.0 g, 1.8 mmol) in 125 mL dichloromethane at −78° C. After 3 hours, the reaction was warmed to room temperature and then quenched with a saturated aqueous sodium sulfate solution. The reaction mixture was filtered through a pad of celite, and the filtrate was concentrated to give a white foam. Triturated with 10% diethyl ether/hexanes to give 0.29 g of the title compound as a white solid; mp 163–168° C.

EXAMPLE 26

Synthesis of [(2,4,6-Triisopropyl-phenyl)-acetyl]-sulfamic acid 4-acetylamino)-2,6-diisopropyl-phenyl ester

[(2,4,6-Triisopropyl-phenyl)-acetyl]-sulfamic acid 4-amino-2,6-diisopropyl-phenyl ester (1.0 g, 1.9 mmol) was mixed with 0.54 mL (3.8 mmol) of triethyl amine in 50 mL of tetrahydrofuran at room temperature. Acetyl chloride (0.14 mL, 1.9 mmol) was added, and the resulting suspension was stirred overnight. Concentrated in vacuo and partitioned the oily residue between 1 M HCl and dichloromethane. Dried the organic layer over magnesium sulfate, filtered, and concentrated to give an orange foam. Chromatography on silica gel (20% ethyl acetate/hexanes) gave 0.56 g of the title compound as a white solid; mp 203–205° C.

EXAMPLE 27

Synthesis of [(2,4,6-Triisopropyl-phenyl)-acetyl]-sulfamic acid 4-(2-hydroxy-ethylamino)-2,6-diisopropyl-phenyl ester

[(2,4,6-Triisopropyl-phenyl)-acetyl]-sulfamic acid 4-amino-2,6-diisopropyl-phenyl ester (1.0 g, 1.9 mmol) was suspended in 50 mL of 1:1 glacial acetic acid/water and a stream of ethylene oxide was bubbled in for 15 minutes. The reaction mixture was sealed and allowed to stir overnight. The reaction mixture was concentrated in vacuo and partitioned between saturated aqueous sodium bicarbonate and dichloromethane. Dried the organic layer over magnesium sulfate, filtered, and concentrated to give an oily solid. Chromatography on silica gel (20% ethyl acetate/hexanes) gave 0.07 g of the title compound as a tan solid; mp 149–152° C.

EXAMPLE 28

Synthesis of [(2,4,6-Triisopropyl-phenyl)-acetyl]-sulfamic acid 4-[bis-(2-hydroxy-ethyl)-amino]-2,6-diisopropyl-phenyl ester When in the procedure of Example 27, glacial acetic acid is used instead of a glacial acetic acid/water mixture and it is heated to 50° C. in a sealed tube for 15 hours, the title compound is obtained; mp 143–146° C.

EXAMPLE 29

Synthesis of [(2,4,6-Triisopropyl-phenyl)-acetyl]-sulfamic acid 4-(3-(2,6-diisopropyl-phenyl)-ureido]-2,6-diisopropyl-phenyl ester When in the procedure of Example 7, ethyl 3-isocyanatopropionate is replaced with 2,6-diisopropylphenyl isocyanate, the title compound is obtained; mp 133–135° C.

EXAMPLE 30

Synthesis of [(2,4,6-Triisopropyl-phenyl)-acetyl]-sulfamic acid 2,6-diisopropyl-4-(3-phenyl-ureido-phenyl ester When in the procedure of Example 7, ethyl 3-isocyanatopropionate is replaced with phenyl isocyanate, the title compound is obtained; mp 185–187° C.

EXAMPLE 31

Synthesis of [(2,4,6-Triisopropyl-phenyl)-acetyl]-sulfamic acid 2,6-diisopropyl-4-(3-phenyl-thioureido]-phenyl ester When in the procedure of Example 7, ethyl 3-isocyanatopropionate is replaced with phenyl isothiocyanate, the title compound is obtained; mp 173–175° C.

EXAMPLE 32

Synthesis of [(2,4,6-Triisopropyl-phenyl)-acetyl]-sulfamic acid 2,6-diisopropyl-4-(thiophene-2-sulfonyamino)-phenyl ester When in the procedure of Example 26, acetyl chloride is replaced with thiophene-2-yl sulfonyl chloride, the title compound is obtained.

EXAMPLE 33

Synthesis of [(2,4,6-Triisopropyl-phenyl)-acetyl]-sulfamic acid 4-(5 dimethylamino-naphthalene-1-sulfonylamino)-2,6-diisopropyl-phenyl ester When in the procedure of Example 26, acetyl chloride is replaced with dansyl chloride, the title compound is obtained; mp 103–105° C.

EXAMPLE 34

Synthesis of [(2,4,6-Triisopropyl-phenyl)-acetyl]-sulfamic acid 2,6-diisopropyl-4methanesulfonylamino-phenyl ester When in the procedure of Example 26, acetyl chloride is replaced with methanesulfonyl chloride, the title compound is obtained; mp 164–166° C.

EXAMPLE 35

Synthesis of [(2,4,6-Triisopropyl-phenyl)-acetyl]-sulfamic acid 2,6-diisopropyl-4-sulfamoyl-phenyl ester Sodium nitrite (0.78 g, 11.3 mmol) in 1.25 mL $H_2O$ was added to a solution of [(2,4,6-triisopropyl-phenyl)-acetyl]- sulfamic acid 4-amino-2,6 diisopropyl-phenyl ester (3.875 g, 7.5 mmol) in 10 mL AcOH and 1.75 mL concentrated HCl. The diazotized solution was stirred for ½ hour before pouring into a saturated solution of $SO_2$ containing 0.25 g of $CuCl_2$ in 20 mL AcOH and 20 mL benzene. After stirring overnight, the solution was poured onto ice water and precipitated [(2,4,6-triisopropyl-phenyl)-acetyl]-sulfamic acid 2,6-diisopropyl-4-sulfonyl chloride-phenyl ester which was collected by filtration, total weight 3.8 9, (84%). Ammonia gas was bubbled through a solution of [(2,4,6-triisopropyl phenyl)-acetyl]-sulfamic acid 2,6-diisopropyl-4-sulfonyl chloride-phenyl ester (1 g, 1.7 mmol) in 10 mL THF. The precipitate was collected and purified by column chromatography (1:1=EtOAc/Hexane), white powder obtained weight 0.5 g; mp 164–166° C.

EXAMPLE 36

Synthesis of 6-(3,5-Diisopropyl-4-{[(2,4,6-triisopropyl-phenyl)-acetyl]sulfamoyloxy}-phenyl)-hexanoic acid ethyl ester When in the procedure of Example 18, 2,6-bis(1-methylethyl)-4-cyanophenyl sulfamate is replaced with 6-(3,5-Diisopropyl-4-sulfamoyloxy-phenyl)-hexanoic acid ethyl ester, the title compound is obtained as a white solid from hexanes, 0.1441 g. Atmospheric pressure CI Mass Spectrum: $[M+H^+]^+=644.4$.

EXAMPLE 37

Synthesis of 6-(3,5-Diisopropyl-4-{[(2,4,6-triisopropyl-phenyl-acetyl]sulfamoyloxy}-phenyl)-hexanoic acid 6-(3,5-Diisopropyl-4-{[(2,4,6-triisopropyl-phenyl-acetyl] sulfamoyloxy}-phenyl)-hexanoic acid ethyl ester (1.52 g, 2.36 mmol) is taken up in methanol (20 mL) and 1N sodium hydroxide solution is added, and the mixture is stirred at room temperature. Water is added to the reaction mixture as the reaction proceeds. The reaction mixture is stirred overnight at room temperature and then concentrated to remove methanol. The resulting mixture is partitioned between ethyl acetate and citric acid solution (10% aqueous, 100 mL). The layers are separated, the organic layer is washed with brine, dried over magnesium sulfate, filtered, and concentrated to an oil. The oil is chromatographed on silica gel (70-230 mesh) using hexanes/ethyl acetate, 1:1, v/v. The product is obtained as a white solid from hexanes, 0.992 g. Atmospheric pressure CI Mass Spectrum: [M-H]=614.4.

We claim:
1. A compound of formula

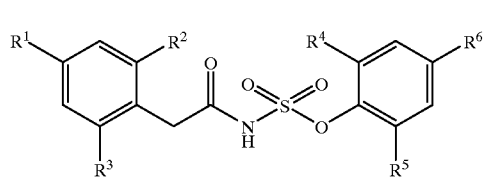

I or a pharmaceutically acceptable salt thereof wherein:
$R^1$ is hydrogen, alkyl, or alkoxy;
$R^2$ to $R^5$ are alkyl, alkoxy, or unsubstituted or substituted phenyl;
$R^6$ is —CN,
—$(CH_2)_{0-1}$—$NR^7R^8$,
—O—$(CH_2)_{1-10}$—Z wherein Z is —$NR^9R^{10}$, $OR^1$, or $CO_2R^1$,
—OC(=O)$R^{11}$,
—$SR^{11}$,
—SCN,
—$S(CH_2)_{1-10}Z$,
—$S(O)_{1-2}R^{12}$ wherein $R^{12}$ is hydroxy, alkoxy, alkyl, $(CH_2)_{1-10}Z$ or $NR^7R^8$,
—C(=O)$XR^{11}$,
—$CH_2$—$R^{13}$ wherein $R^{13}$ is $(CH_2)_{0-5}$—Y—$(CH_2)_{0-5}Z$, or wherein $R^7$ and $R^8$ are each independently selected from:
—hydrogen, at least one of $R^7$ and $R^8$ is other than hydrogen,
—$(CH_2)_{1-10}Z$ wherein Z is as above and $R^9$ and $R^{10}$ are each independently selected from hydrogen, alkyl, and unsubstituted or substituted phenyl, or
$R^9$ and $R^{10}$ are taken together with the nitrogen to which they are attached to form a ring selected from:
—$(CH_2)_2$—O—$(CH_2)_2$,
—$(CH_2)_2$—S—$(CH_2)_2$,
—$(CH_2)_2$—$CR^{14}R^{15}$—$(CH_2)_{1-2}$, and
—$(CH_2)_2$—$NR^{16}$—$(CH_2)_2$, wherein
$R^{14}$, $R^{15}$, and $R^{16}$ are each independently selected from hydrogen, alkyl, and unsubstituted or substituted phenyl;
—C(=Q)$XR^{11}$ wherein X is a bond or NH wherein Q is O or S,
$R^{11}$ is hydrogen, alkyl, unsubstituted or substituted phenyl,
—$(CH_2)_{0-5}$—Y—$(CH_2)_{0-5}Z$ wherein Z is as defined above and Y is phenyl or a bond;
—C(=O)$CR^{17}R^{18}Z$;
—C(=O)$NRCR^{17}R^{18}Z$ wherein $R^{17}$ and $R^{18}$ are each independently hydogen, alkyl, phenyl, substituted phenyl, or the side chain of a naturally occurring amino acid;
—$S(O)_{1-2}R^{19}$ wherein $R^{19}$ is alkyl, unsubstituted or substituted phenyl, naphthyl, or a heteroaromatic ring, or $NR^9R^{10}$ or
$R^7$ and $R^8$ are taken together with the nitrogen to which they are attached to form a ring:
—$(CH_2)_2$—O—$(CH_2)_2$—,
—$(CH_2)_2$—S—$(CH_2)_2$—,
—$(CH_2)_2$—$CR^{14}R^{15}$—$(CH_2)_{1-2}$—,
—$(CH_2)_2$—$NR^{16}$—$(CH_2)_2$— wherein $R^{14}$, $R^{15}$, and $R^{16}$ are as above.

2. A compound according to claim 1 wherein:
$R^1$ is hydrogen or alkyl of from 1 to 4 carbon atoms;
$R^2$ to $R^5$ are each alkyl of from 1 to 4 carbon atoms;
$R^6$ is —$NR^7R^8$ wherein $R^7$ and $R^8$ are each independently selected from:
hydrogen, at least one of $R^7$ and $R^8$ is not hydrogen,
—$(CH_2)_{1-10}Z$,
—C(=Q)$XR^{11}$, or
—$S(O)_{1-2}R^{19}$.

3. A compound according to claim 2 wherein:
$R^7$ is hydrogen and
$R^8$ is —C(=O)$CR^{17}R^{18}Z$ wherein Z is $NH_2$, wherein one of $R^{17}$ or $R^{18}$ is the side chain of a naturally occurring amino acid and the other is hydrogen.

4. A compound according to claim 2 wherein:
$R^1$ is hydrogen or alkyl of from 1 to 4 carbon atoms;
$R^2$ to $R^5$ are each alkyl of from 1 to 4 carbon atoms;
$R^6$ is $NR^7R^8$ wherein one of $R^7$ is hydrogen and the $R^8$ is $S(O)_{1-2}R^{19}$.

5. A compound according to claim 1 wherein:
$R^1$ is hydrogen or alkyl of from 1 to 4 carbon atoms;
$R^2$ to $R^5$ are each alkyl of from 1 to 4 carbon atoms;
$R^6$ is $NR^7R^8$ wherein $R^7$ and $R^8$ taken together with the nitrogen to which they are attached to form a ring:
—$(CH_2)_2$—O—$(CH_2)_2$—,
—$(CH_2)_2$—S—$(CH_2)_2$—,
—$(CH_2)_2$—$CR^{14}R^{15}$—$(CH_2)_2$— wherein $R^{14}$ and $R^{15}$ are each independently selected from hydrogen, alkyl, or phenyl, or
—$(CH_2)_2$—$NR^{16}$—$(CH_2)_2$— wherein $R^{16}$ is hydrogen, alkyl, or phenyl.

6. A compound according to claim 1 wherein:
$R^1$ is hydrogen or alkyl of from 1 to 4 carbons,
$R^2$ to $R^5$ an alkyl of from 1 to 4 carbons, and
$R^6$ is —C(=O)$XR^{11}$ or —$CH_2$—$R^{13}$.

7. A compound according to claim 1 wherein:
$R^1$ is hydrogen or alkyl of from 1 to 4 carbon atoms;
$R^2$ to $R^5$ are alkyl of from 1 to 4 carbon atoms;
$R^6$ is —O—$(CH_2)_{1-10}Z$,
—O—C (=O)$R^{11}$,
—SH,
—SCN,
—S$(CH_2)_{1-10}Z$, or
—S(O)$_{1-2}R^{12}$.

8. A compound according to claim 6 wherein:
$R^1$ is hydrogen or alkyl of from 1 to 4 carbon atoms;
$R^2$ to $R^5$ are alkyl of from 1 to 4 carbon atoms;
$R^6$ is O$(CH_2)_{1-10}NR^9R^{10}$.

9. A compound according to claim 1 and selected from:
(S)-[5-tert-Butoxycarbonylamino-5-(3,5-diisopropyl-4-{[(2,4,6-triisopropyl-phenyl)-acetyl]sulfamoyloxy}-phenylcarbamoyl)-pentyl]-carbamic acid tert-butyl ester;
(S)-[(2,4,6-Triisopropyl-phenyl)-acetyl]-sulfamic acid 4-(2,6-diamino-hexanoylamino)-2,6-diisopropyl-phenyl ester dihydrochloride;
[(2,4,6-Triisopropyl-phenyl)-acetyl]-sulfamic acid 4-(2-t-butoxycarbonylamino-acetylamino)-2,6-diisopropyl-phenyl ester;
[(2,4,6-Triisopropyl-phenyl)-acetyl]-sulfamic acid 4-(2-amino-acetylamino)-2,6-diisopropyl-phenyl ester;
[(2,4,6-Triisopropyl-phenyl)-acetyl]-sulfamic acid 4-(2-t-butoxycarbonylamino-4-methylsulfanyl-butyrylamino)-2,6-diisopropyl-phenyl ester;
[(2,4,6-Triisopropyl-phenyl)-acetyl]-sulfamic acid 4-(2-amino-4-methylsulfanyl-butyrylamino)-2,6-diisopropyl-phenyl ester trifluoroacetate;
3-[3-(3,5-Diisopropyl-4-{[(2,4,6-triisopropyl-phenyl)-acetyl]sulfamoyloxy}-phenyl)-ureido]-propionic acid ethyl ester;
3-[3-(3,5-Diisopropyl-4-{[(2,4,6-triisopropyl-phenyl)-acetyl]sulfamoyloxy}-phenyl)-ureido]-propionic acid;
[(2,4,6-Triisopropyl-phenyl)-acetyl]-sulfamic acid 4-[2-amino-3-(1H-indol-3-yl)-propionylamino]-2,6-diisopropyl-phenyl ester;
[(2,4,6-Triisopropyl-phenyl)-acetyl]-sulfamic acid 4-(5-amino-pentanoylamino)-2,6-diisopropyl-phenyl ester trifluoroacetate(1:1)(salt);
(D)-[(2,4,6-Triisopropyl-phenyl)-acetyl]-sulfamic acid 4-(2-amino-propionylamino)-2,6-diisopropyl-phenyl ester trifluoroacetate(1:1) (salt);
(L)-[(2,4,6-Triisopropyl-phenyl)-acetyl]-sulfamic acid 4-(2-amino-propionylamino)-2,6-diisopropyl-phenyl ester;
[(2,4,6-Triisopropyl-phenyl)-acetyl]-sulfamic acid 4-(2-amino-2-methyl-propionylamino)-2,6-diisopropyl-phenyl ester;
[(2,4,6-Triisopropyl-phenyl)-acetyl]-sulfamic acid 4-(3-dimethylamino-propoxy)-2,6-diisopropyl-phenyl ester;
[(2,4,6-Triisopropyl-phenyl)-acetyl]-sulfamic acid 4-(3-dimethylamino-propoxy)-2,6-diisopropyl-phenyl ester hydrochloride salt;
[(2,4,6-Triisopropyl-phenyl)-acetyl]-sulfamic acid 4-(3-amino-propoxy)-2,6-diisopropyl-phenyl ester hydrochloride salt;
[(2,4,6-Triisopropyl-phenyl)-acetyl]-sulfamic acid 2,6-diisopropyl-4-thiocyanato-phenyl ester;
[(2,4,6-Triisopropyl-phenyl)-acetyl]-sulfamic acid 4-cyano-2,6-diisopropyl-phenyl ester;
[(2,4,6-Triisopropyl-phenyl)-acetyl]-sulfamic acid 4-[(2-amino-acetylamino)-methyl]-2,6-diisopropyl-phenyl ester;
[(2,4,6-Triisopropyl-phenyl)-acetyl]-sulfamic acid 4-formyl-2,6-diisopropyl-phenyl ester;
[(2,4,6-Triisopropyl-phenyl)-acetyl]-sulfamic acid 4-(2-cyano-vinyl)-2,6-diisopropyl-phenyl ester;
[(2,4,6-Triisopropyl-phenyl)-acetyl]-sulfamic acid 4-(benzylamino-methyl)-2,6-diisopropyl-phenyl ester mono hydrochloride;
[(2,4,6-Triisopropyl-phenyl)-acetyl]-sulfamic acid 2,6-diisopropyl-4-(4-methyl-piperazin-1-ylmethyl)-phenyl ester, dihydrochloride;
[(2,4,6-Triisopropyl-phenyl)-acetyl]-sulfamic acid 4-carbamoyl-2,6-diisopropyl-phenyl ester;
[(2,4,6-Triisopropyl-phenyl)-acetyl]-sulfamic acid 4-hydroxymethyl-2,6-diisopropyl-phenyl ester;
[(2,4,6-Triisopropyl-phenyl)-acetyl]-sulfamic acid 4-acetylamino-2,6-diisopropyl-phenyl ester;
[(2,4,6-Triisopropyl-phenyl)-acetyl]-sulfamic acid 4-(2-hydroxy-ethylamino)-2,6-diisopropyl-phenyl ester;
[(2,4,6-Triisopropyl-phenyl)-acetyl]-sulfamic acid 4-[bis-(2-hydroxy-ethyl)-amino]-2,6-diisopropyl-phenyl ester;
[(2,4,6-Triisopropyl-phenyl)-acetyl]-sulfamic acid 4-[3-(2,6-diisopropyl-phenyl)-ureido]-2,6-diisopropyl-phenyl ester;
[(2,4,6-Triisopropyl-phenyl)-acetyl]-sulfamic acid 2,6-diisopropyl-4-(3-phenyl-ureido]-phenyl ester;
[(2,4,6-Triisopropyl-phenyl)-acetyl]-sulfamic acid 2,6-diisopropyl-4-(3-phenyl-thioureido]-phenyl ester;
[(2,4,6-Triisopropyl-phenyl)-acetyl]-sulfamic acid 2,6-diisopropyl-4-(thiophene-2-sulfonyl-amino)-phenyl ester;
[(2,4,6-Triisopropyl-phenyl)-acetyl]-sulfamic acid 4-(5-dimethylamino-naphthalene-1-sulfonylamino)-2,6-diisopropyl-phenyl ester;
[(2,4,6-Triisopropyl-phenyl)-acetyl]-sulfamic acid 2,6-diisopropyl-4-methanesulfonylamino-phenyl ester;
[(2,4,6-Triisopropyl-phenyl)-acetyl]-sulfamic acid 2,6-diisopropyl-4-sulfamoyl-phenyl ester;
6-(3,5-Diisopropyl-4-{[(2,4,6-triisopropyl-phenyl-acetyl]sulfamoyloxy}-phenyl)-hexanoic acid ethyl ester; and
6-(3,5-Diisopropyl-4-{[(2,4,6-triisopropyl-phenyl-acetyl]sulfamoyloxy}-phenyl)-hexanoic acid.

10. A pharmaceutical composition comprising a therapeutically effective amount of a compound of claim 1 and a pharmaceutically acceptable carrier.

11. A method of treating hypercholesterolemia comprising administering to a mammal in need of said treatment a therapeutically effective amount of a compound of claim 1.

12. A method of treating atherosclerosis comprising administering to a mammal in need of said treatment a therapeutically effective amount of a compound of claim 1.

13. A method of regulating plasma cholesterol concentrations comprising administering to a mammal in need of said treatment a therapeutically effective amount of a compound according to claim 1.

14. A method for lowering the serum or plasma level of Lp(a) in a mammal in need of said treatment, comprising administering to said mammal an amount effective for lowering the serum or plasma level of said Lp(a) of a compound according to claim 1.

15. A method of treating peripheral vascular disease comprising administering to a mammal in need of said treatment a therapeutically effective amount of a compound according to claim 1.

16. A method of treating restenosis comprising administering to a mammal in need of said treatment a therapeutically effective amount of a compound according to claim 1.

* * * * *